(12) United States Patent
Meng et al.

(10) Patent No.: US 9,839,478 B2
(45) Date of Patent: Dec. 12, 2017

(54) METHOD FOR TREATING LOWER EXTREMITY VARICOSE VEIN COMBINED ULTRASONIC WAVE AND MICROWAVE

(71) Applicant: Beijing TransEasy Medical Tech.Co., Ltd., Beijing (CN)

(72) Inventors: Kai Meng, Beijing (CN); Qingyi Meng, Beijing (CN); Jinxiu Huang, Beijing (CN); Jie Sun, Beijing (CN); Xiaoping Wang, Beijing (CN)

(73) Assignees: Kai Meng, Beijing (CN); Jie Sun, Beijing (CN)

( * ) Notice: Subject to any disclaimer, the term of this patent is extended or adjusted under 35 U.S.C. 154(b) by 0 days.

(21) Appl. No.: 14/201,916

(22) Filed: Mar. 9, 2014

(65) Prior Publication Data

US 2014/0188102 A1 Jul. 3, 2014

Related U.S. Application Data

(63) Continuation-in-part of application No. 13/726,037, filed on Dec. 22, 2012.

(51) Int. Cl.
| | |
|---|---|
| *A61B 18/18* | (2006.01) |
| *A61B 8/08* | (2006.01) |
| *A61B 8/13* | (2006.01) |
| *A61B 8/00* | (2006.01) |
| *A61N 5/04* | (2006.01) |
| *A61B 18/00* | (2006.01) |

(52) U.S. Cl.
CPC ............ *A61B 18/1815* (2013.01); *A61B 8/13* (2013.01); *A61B 8/463* (2013.01); *A61B 8/488* (2013.01); *A61B 8/54* (2013.01); *A61B 8/546* (2013.01); *A61B 2018/00404* (2013.01); *A61B 2018/00589* (2013.01); *A61B 2018/00982* (2013.01); *A61B 2018/00994* (2013.01); *A61N 5/04* (2013.01)

(58) Field of Classification Search
None
See application file for complete search history.

(56) References Cited

U.S. PATENT DOCUMENTS 5,437,664 A * 8/1995 Cohen et al. .................. 606/42
5,762,066 A * 6/1998 Law et al. .................. 600/439
(Continued)

*Primary Examiner* — Jennifer Dieterle
*Assistant Examiner* — Kevin Pontius

(57) ABSTRACT

A method for treating the lower extremity varicose vein combined ultrasonic wave and microwave is provided. The method includes steps of firstly finding the diseased vein by the ultrasonic imaging equipment; and then directly effecting the microwave treatment catheter/needle on the diseased vein; by the concentric thermal coagulation release effect of the microwave to the tissue, instantly generating high temperature with the certain penetration range in a small range for tissue coagulation; and then gradually making the vascular fibrosis; finally making the completely atresia, thus achieving the therapeutic aim. The present invention uses the ultrasonic imaging microwave treatment technique to treat the lower extremity varicose vein disease. It accurately, firmly and thoroughly closes the varicose blood vessel, has the exact effect, small trauma and less pain to patients, less bleeding in surgery, quick recovery, simple operative procedure and no significant complication, is difficult to form the deep venous thrombosis.

2 Claims, 4 Drawing Sheets

(56) References Cited

U.S. PATENT DOCUMENTS

| | | | |
|---|---|---|---|
| 2005/0015123 A1* | 1/2005 | Paithankar | A61B 18/24 607/88 |
| 2006/0189979 A1* | 8/2006 | Esch | A61B 18/1477 606/49 |
| 2008/0147056 A1* | 6/2008 | van der Weide et al. | 606/33 |
| 2010/0185087 A1* | 7/2010 | Nields et al. | 600/439 |
| 2012/0143180 A1* | 6/2012 | Lee et al. | 606/33 |
| 2013/0006229 A1* | 1/2013 | Delaney | A61B 18/042 606/15 |
| 2013/0102862 A1* | 4/2013 | Mercader et al. | 600/317 |

* cited by examiner

METHOD FOR TREATING LOWER EXTREMITY VARICOSE VEIN COMBINED ULTRASONIC WAVE AND MICROWAVE

CROSS-REFERENCE TO RELATED APPLICATION

This is a Continuation-In-Part application of U.S. patent application Ser. No. 13/726,037, filed on Dec. 22, 2012.

BACKGROUND OF THE PRESENT INVENTION

Field of Invention

The present invention relates to a treatment technique for the body's thermal ablation, and more particularly to a method for treating the lower extremity varicose vein combined ultrasonic wave and microwave.

Description of Related Arts

In the medical vascular surgery field, the lower extremity varicose vein is also called as the lower extremity vein insufficiency, and is a common seen and frequently occurring disease with high incidence. Its main clinical manifestations are soreness, numbness, itching, sense of heaviness and tiredness from the affected limb. While the patient standing, the superficial vein of the affected limb swells, expands, detours and even curls into a group. The severe patient will be complicated with thrombophlebitis; and the pigmentation, atrophy, eczema, ulcer, acute hemorrhage and so on will occur on the skin of the affected limb. It mainly results from venous valve insufficiency, weak venous wall, continuously increased intravenous pressure and so on, in such a manner that the flood reversely flows towards the lower extremity distal direction, so that the superficial vein is varicose. Classified from anatomy, the lower extremity venous system is made up of the superficial venous system, the deep venous system and the perforating venous system. The venous valve insufficiency, the weak venous wall and the continuously increased intravenous pressure are likely pathogenic, which results in pathological changes and clinical manifestations. This disease mostly occurs in the person engaging in the long standing long squatting work, and the person with high-intensity physical activity. Pregnancy, chronic cough, long-term constipation and so on can cause the continuously increased intravenous pressure, so that the vein has the varicose symptom. Furthermore, approximately 70% of patients with the disease have the genetic predisposition. The concrete manifestations are that the lower extremity meanderingly expands, the superficial varicose vein is tortuously earthworm-like, and the symptom of the leg is more significant than that of the thigh, more obvious while standing, and reduced or disappeared after raising the leg. Simultaneously, the affected extremity has the soreness, pain, numbness and other abnormal sensations. At the early period, the affected extremity has discomfortable soreness and heavy hypodynamia, is significant while standing, and is reduced while walking, lying supine or lifting the limb, or even has the pain. At the late period, due to congestion, skin nutrition disorders, so that the skin of the leg atrophying, desquamating, itching, and pigmentation, the skin subcutaneous tissue induration, thrombus, phlebitis, eczema, and chronic ulcer (commonly known as "old rotten feet") occur. It is possible for the dermal chronic ulcer to be cancerous.

Currently, the traditionally Chinese treatment method is the surgical treatment using surgery, which has been nearly a hundred years of history, and mainly includes large (small) saphenous venous high ligation, communicating branch ligation, large (small) saphenous and varicose vein stripping surgery. It mainly includes three steps of: highly ligating the large (small) saphenous vein, stripping the varicose vein and ligating, cutting off the perforating vein. Due to large traumas, a lot of pain, slow recovery, longer hospitalization, postoperative skin scar, great risk of infection, greater surgical risk and other shortcomings, this method is not easy to be accepted by the patient. In recent years, the surgery treatment has been gradually replaced by the minimally invasive surgical treatment. The popular minimally invasive surgeries at home and abroad are mainly: Transilluminated Powered Phlebectomy (TIPP), Endo Venous Laser Treatment (EVLT), Endovenous radiofrequency closure technique and Subfascial Endoscopic Perforator Surgery, SEPS). The shortcomings of the existing minimally invasive surgery are mainly: 1. due to different physical energy, the lesion vessel can not be firmly closed, thereby it is relatively easy to relapse and develop thrombosis; 2. limited indications, which is adapted for mild illness and can not simultaneously treat the leg ulcer caused by the perforating venous insufficiency; 3. complicated operation; 4. the laser machine is just a single machine without timely monitoring of color Doppler ultrasound, the treatment is more blind, and the effect can not be immediately inspected; 5. more expensive equipment.

SUMMARY OF THE PRESENT INVENTION

To overcome the above mentioned shortcomings of the method for treating the lower extremity varicose disease by minimally invasive surgery in the prior art, the present invention provides a method for treating the lower extremity varicose disease combined ultrasonic wave and microwave.

The method for treating the lower extremity varicose disease combined ultrasonic wave and microwave in the present invention, is characterized by: firstly finding the diseased vein by the ultrasonic imaging equipment; and then directly effecting the microwave treatment catheter/needle on the diseased vein; by the concentric thermal coagulation release effect of the microwave to the tissue, instantly generating high temperature with the certain penetration range in a small range for tissue coagulation; and then gradually making the vascular fibrosis; finally making the completely atresia, thus achieving the therapeutic aim.

The method of the present invention is adapted for treating the great saphenous varicose vein, the small saphenous varicose vein, the cluster varicose vein, superficial hemangioma, the perforator vein insufficiency accompanied by lower extremity ulcer disease or calf vein ulcer.

Compared with the prior art, the method for treating the lower extremity varicose disease combined ultrasonic wave and microwave of the present invention has the beneficial effects as follows.

The present invention uses the ultrasonic imaging microwave treatment technique to treat the lower extremity varicose vein disease, which accurately, firmly and thoroughly closes the varicose blood vessel, has the exact effect, has small trauma and less pain to patients, less bleeding in surgery, quick recovery, is difficult to form the deep venous thrombosis and safe, has simple operative procedure and no significant complication. Under the whole monitoring of color Doppler ultrasound, this minimally invasive surgery is implemented, which is capable of accurately treating the diseased blood vessel, and simultaneously instantly verifying the surgical treatment effect.

Figure 1:
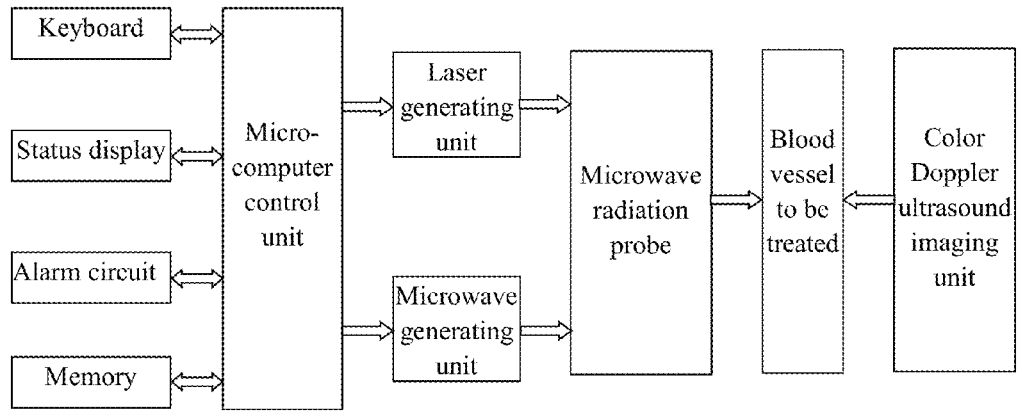
FIG. 1 is a block diagram of an ultrasonic imaging microwave therapeutic apparatus according to a preferred embodiment of the present invention.

In the drawings, 31—resonant cavity input lens; 32—nonlinear optical crystal; 33—laser medium; 34—resonant cavity output lens; 35—output direction; 71—front probe part; 72—rear probe part; 73—microwave emission hole; 74—conduit; 75—laser interface; 76—temperature signal interface; 77—microwave interface.

DETAILED DESCRIPTION OF THE PREFERRED EMBODIMENT

The present invention is further explained in detail with the accompanying drawings.

Example 1: Ultrasonic Imaging Microwave Therapeutic Apparatus

Figure 2:
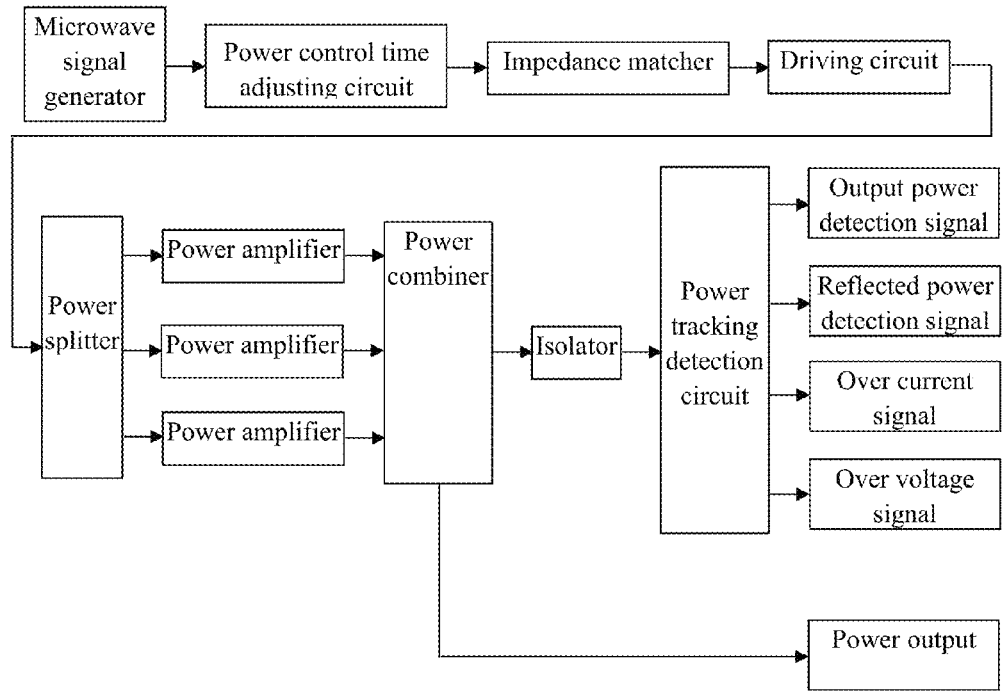
FIG. 2 is a circuit diagram of a microwave generating unit according to the above preferred embodiment of the present invention.
Figure 3:
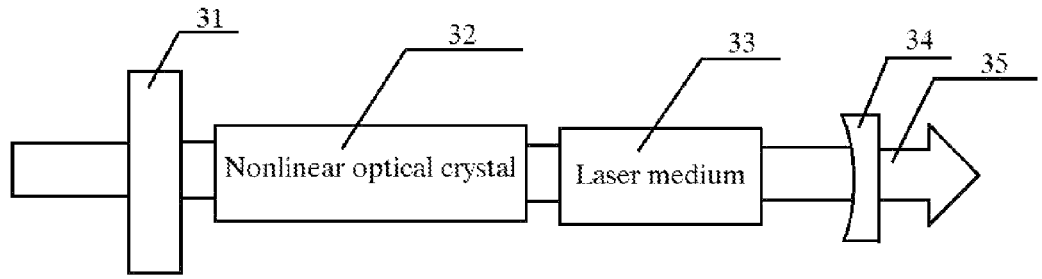
FIG. 3 is a block diagram of a laser generating unit according to the above preferred embodiment of the present invention.
Figure 4:
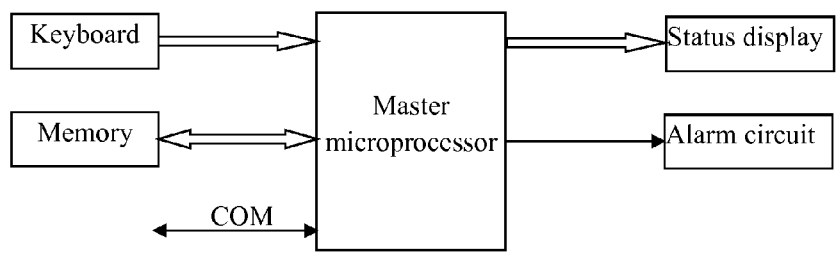
FIG. 4 is a circuit diagram of a microcomputer control unit according to the above preferred embodiment of the present invention.
Figure 5:
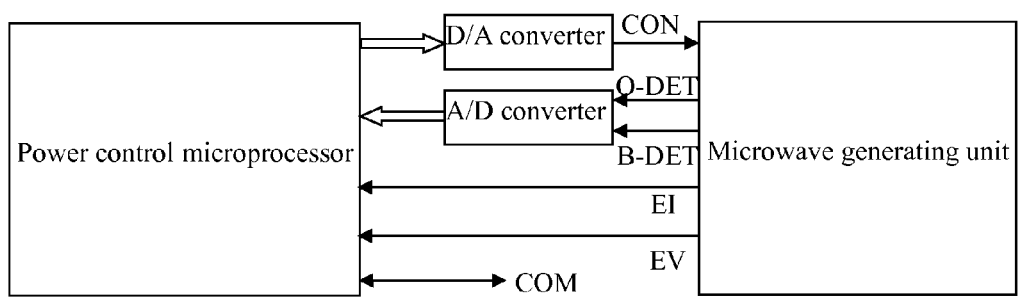
FIG. 5 is a circuit diagram of a power control microprocessor according to the above preferred embodiment of the present invention.
Figure 6:
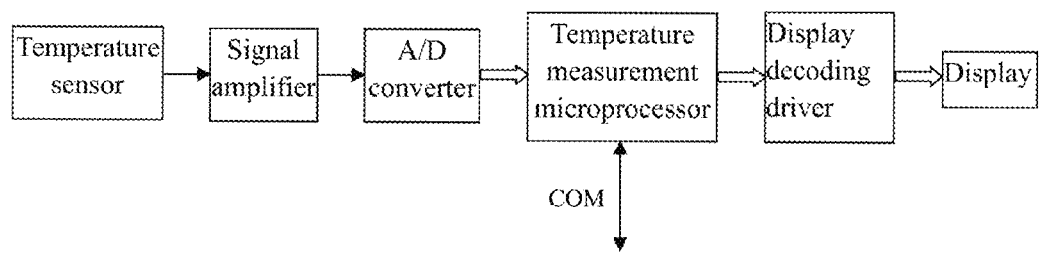
FIG. 6 is a circuit diagram of a temperature measurement microprocessor according to the above preferred embodiment of the present invention.
Figure 7:
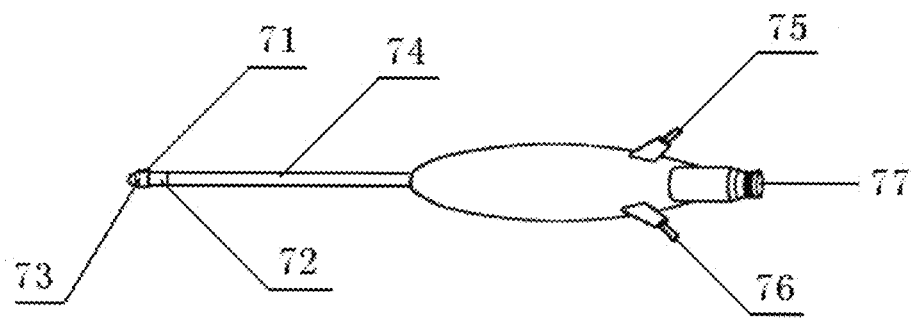
FIG. 7 is a schematic diagram of a microwave radiation probe according to the above preferred embodiment of the present invention.

Referring to FIG. 1 of the drawings, an ultrasonic imaging microwave therapeutic apparatus according to a preferred embodiment of the present invention is illustrated, wherein the ultrasonic imaging microwave therapeutic apparatus comprises a microwave radiation probe (as shown in FIG. 7), a microwave generating unit (as shown in FIG. 2), a laser generating unit (as shown in FIG. 3), a color Doppler ultrasound imaging unit, and a microcomputer control unit (as shown in FIGS. 4-6).

The microwave radiation probe comprises a front probe part 71, a rear probe part 72 and a probe interface part. A microwave emission hole 73 is provided at the front probe part 71. A laser cursor is provided at the rear probe part 72. The rear probe part 72 of the microwave radiation probe has a hollow structure. A wire for the transmission of microwave and a cable for the transmission of laser are provided within the rear probe part 72 of the microwave radiation probe. The rear probe part 72 of the microwave radiation probe is sealedly connected with a conduit 74 having the wire and the cable. The conduit 74 is connected with the probe interface part. A laser interface 75 connected with a port of the laser generating unit and a microwave interface 77 connected with a coaxial output terminal of the microwave generating unit are provided at the probe interface part. A temperature sensor is located within the hollow structure of the rear probe part 72 of the microwave radiation probe. A temperature signal transmission line is located within the conduit 74. A temperature signal interface 76 is provided at the probe interface part.

A power output of the microwave generating unit is connected with the probe interface part to provide a microwave signal for ablation treatment of lower extremity varicose vein. The microwave generating unit comprises a microwave signal generator, a power control time adjusting circuit, an impedance matcher, a driving circuit, a power splitter, a plurality of power amplifiers, a power combiner, an isolator and a power tracking detection circuit. The power tracking detection circuit outputs an output power detection signal, a reflected power detection signal, an over current signal and an over voltage signal.

The laser generating unit, adapted for providing a laser signal which is used to identify a wavelength range of visible light of the microwave probe, comprises an InGaAs infrared laser pump, and a laser cavity. A laser medium 33 and a nonlinear optical crystal 32 are provided within the laser cavity along a same axis. The laser medium 33 is $YVO_4$ crystal doped with $Nd^{3+}$, wherein a doping concentration of $Nd^{3+}$ is 2.5-7.2 at %. The nonlinear optical crystal 32 is KTP crystal.

The color Doppler ultrasound imaging unit, adapted for obtaining the dynamic display of the image of the tissue to be treated and the dynamic display of the image of the tissue while treating, comprises a color Doppler ultrasound host and a color Doppler ultrasound control panel.

The microcomputer control unit outputs a microwave power control signal to control and adjust the power control of the microwave generating unit. The microcomputer control unit outputs a laser control signal to control the switch-on/off of the laser generating unit. The microcomputer control unit comprises a master microprocessor, a power control microprocessor, and a temperature measurement microprocessor, wherein the master microprocessor is connected with the power control microprocessor and the temperature measurement microprocessor via a communication interface COM. The output power detection signal O-DET and the reflected power detection signal B-DET of the microwave generating unit are transformed by an A/D converter, and then sent to the power control microprocessor. The over current signal EI and the over voltage signal EV of the microwave generating unit are inputted into the power control microprocessor. The power control signal CON of the microwave generating unit comes from an output of the D/A converter connecting with the power control microprocessor. According to the value of the output power detection signal, the value of the power control signal is obtained by the power control microprocessor. The reflected power detection signal, the over current signal and the over voltage signal are processed by the power control microprocessor, and then inputted into the master microprocessor by the communication interface, and an alarm circuit is started by the master microprocessor for generating an alarm signal. A temperature signal sensed by the temperature sensor is sent to a signal amplifier. An output of the signal amplifier is transformed by the A/D converter, and then sent to the temperature measurement microprocessor. A temperature value outputted by the temperature measurement microprocessor is displayed by a status display. The master microprocessor is further connected with a keyboard, the status display, the alarm circuit and a memory. The keyboard is adapted for inputting a control instruction to the master microprocessor. The status display is adapted for displaying a working state. The alarm circuit is adapted for generating the alarm signal. The memory is adapted for storing set values and temporary data at work.

The therapeutic apparatus provided by the present invention has been applied to hospitals in Shanghai and treated more than 10000 cases of patients. Now, it is evaluated from the following several aspects based on the beneficial effects of the present invention.

(1) Anesthesia and operation time: an average time of the endovascular microwave coagulation operation time every limb is 15 minutes. The therapeutic apparatus of the present invention has short duration of anesthesia, less anesthetic dosage and rapid recovery.

(2) The intraoperative blood loss is average 2.5 ml.

(3) Postoperative symptom improvement, out of bed activity, the hospitalization time of patients: Patients have not wound and lower limb pains. Only postoperative individual cases have foot temporary mild swelling. Patients can ambulate themselves at 1-2 hours after surgery (or according to anesthesia requirements). The average hospitalization time is 5.3 days.

(4) Changes in appearance of the affected limb: The lower extremity varicose veins disappear, clinical symptoms are obviously improved, limb swelling is reduced, pigmentation is gradually faded, and leg ulcers and skin nutrition disorders are obviously improved or healed.

(5) Complications and recurrence: no deep vein thrombosis, pulmonary embolism or other serious complications occur. Calf skin numbness after the surgery is lighter, the average regression time is 2.5 months, the recurrence rate is lower and about 2% (which is lower than that of other methods).

(6) The postoperative color Doppler ultrasound image of lower extremity venous changes, thus it is proved that the effect is good.

In the immediate patients' postoperative day, the diameter of lower extremity saphenous vein is obviously narrowed, no blood flow displays, it can be seen that the spot, light band and vessel wall having thrombosis strong echo within the lumen are obviously thickened and roughened by two-dimensional ultrasound, and the integrity is destroyed. At two weeks after operation, the intraluminal fibrosis is formed on the foregoing basis, and the interior of the lumen is completely closed.

Example 2: Method for Treating Lower Extremity Varicose Vein Combined Ultrasonic Wave and Microwave Embodiment 1

Aiming at treating the lower extremity superficial venous insufficiency, the treatment method of this embodiment comprises steps as follows:
1. Pre-Operative Preparation:
1.1 Patient Preparation:
(1) Check the function of the heart, the lung, the liver, the kidney and other major organs;
(2) Check the lower extremity deep vein graft patency and the valvular function, such as color Doppler ultrasound and venography; simultaneously, position and mark the confluence of the femoral saphenous vein;
(3) Prepare skin on the preoperative day whose upper portion and the belly are flat and lower portion reaches the foot (including the perineum), wherein be careful not to involve in operating the surface skin of the varicose vein while shaving the hair, otherwise the operation should be delayed;
(4) Mark the behaviors of the varicose great saphenous vein and its tributaries on the skin by methyl violet (gentian violet) or methylene blue, mark the incision site, wherein if the surgery is operated on two sides at the same time, the preparation is needed at two sides;
(5) Anesthetize according to the varicose degree of the saphenous vein and the general condition of the patient;
1.2 Instrument Preparation
(1) Turn on the power supply of the ultrasound microwave therapeutic instrument, and check whether the device is in the normal state;
(2) a) Connect the therapeutic catheter with the microwave output terminal and the laser output terminal of the equipment via the microwave output cable and the laser output line, respectively, and connect the foot switch; b) connect the therapeutic needle with the microwave output terminal of the equipment via the microwave output cable, and insert one end of the foot switch into the foot switch position of the microwave equipment;
(3) a) Tightly connect the in and out ports of the therapeutic catheter/needle refrigerant pipe with the in and out ports of the long water pipe, respectively; b) put the segment of the long water pipe with the steel needle at the left side of the pump head and insert the steel needle into the brine bottle (ice water below 15° C.), and hang the brine bottle at the side of the pump head upside down; c) 180°-anticlockwise flip the flipping rod on the pump head for opening the upper briquetting, naturally put the silicone tube in the long water pipe between the roller and the upper briquetting, 180°-clockwise flip the flipping rod for downwardly pressing the upper briquetting into place;
(4) Turn on the peristaltic pump switch and check whether the water cycle is normal;
2. Surgical Procedures:

Routinely clean and disinfect the lesion location of the patient in the supine position; find the confluence of the groin and the femoral saphenous vein of the affected limb by the ultrasound, notch for 1-2 cm at this position (or 0.5-1 cm at the ankle), insert the vein varicose microwave therapeutic catheter under the guidance of laser cursor into the saphenous vein till the ankle from 2 cm below the start of the femoral saphenous vein (if the once insert can not be achieved, insert from the ankle into the proximal end); according to the vein inner diameter width of the affected limb and the body fat or thin, select the appropriate microwave transmission power (50-70 W) and the solidification time (5-10 s), depress the foot switch, solidify point by point and retreat step by step under the ultrasound real-time monitoring. Every time intermittently treat at the interval of 1 cm, slowly exit the wire, compress along the traveling of the saphenous vein by hand, and successively piecewisely solidify close the whole saphenous vein; if the therapeutic wire is blocked, the small incision (vein puncture) is made along the wire at the saphenous vein, and the wire is anterogradely inserted for treating by the same method;

The varicose conglobated branch can travel along the preoperative marked varicose saphenous vein, make the multi vein puncture by the short probe needle via the skin in the ultrasonic real-time monitoring, the microwave transmit power is 30-40 W, and exit the rapid solidification; gradually completely treat the marked varicose vein;

3. Postoperative Treatment:

(1) Observe the edema pain situation of the affected limb and vital signs at the end of operation;

(2) Elevate the affected limb for 20-30° so that the lower limb is slightly higher than the heart in the supine position for being beneficial to blood return; the bandage has uniform pressure for avoiding hematocele and bleeding; extend and flex the ankle on the bed in such a manner that the deep venous blood is extruded by the muscle group so that the blood return is accelerated, which is beneficial to avoid forming the deep venous thrombosis;

(3) Walk on the flat ground out of bed for 1-2 h after postoperative 6 h;

(4) Use the anticoagulants for avoiding forming the postoperative thrombus;

(5) after surgery, firstly wear the elastic stockings and then bandage the affected limb by the elastic bandage on the elastic stockings till postoperative 1-2 weeks, and then wear the elastic stockings for 1-2 months.

Figure 8:
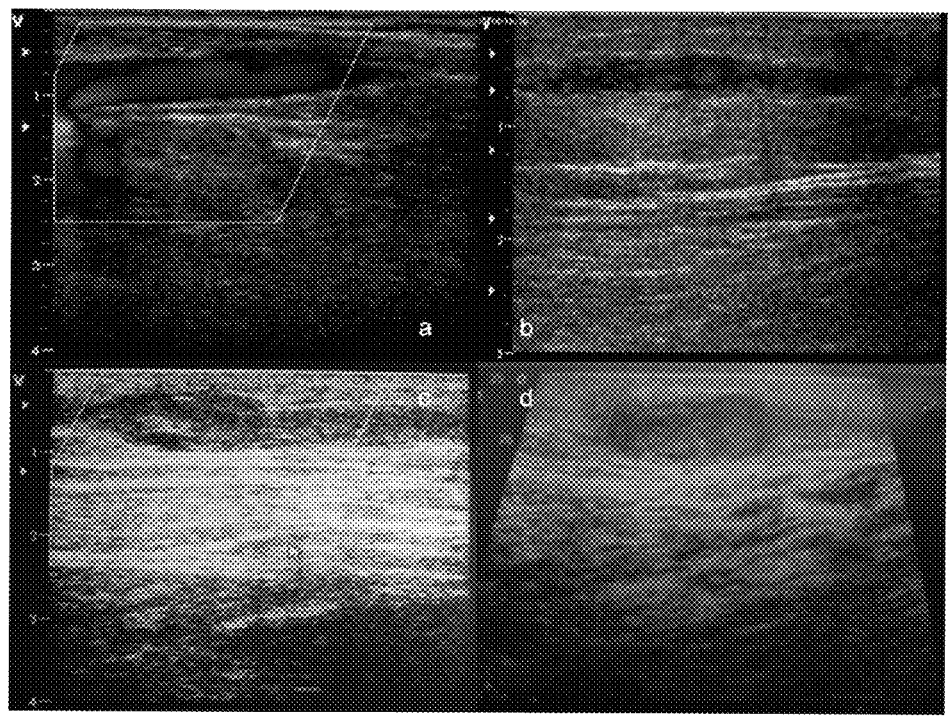
FIG. 8 is an effect drawing of treating the lower extremity superficial venous insufficiency by combining ultrasonic wave and microwave according to a first preferred embodiment of the present invention.

FIG. 8 is the effect drawing which shows the limb superficial venous insufficiency under the ultrasound microwave integrated therapy, wherein a is the color Doppler ultrasound drawing of the preoperative varicose vein, the saphenous vein lumen of the affected limb is enlarged, the blood flow is obvious; b shows at the postoperative second day, the saphenous vein lumen of the affected limb is narrowed, the blood flow is not shown; c shows at the postoperative 2 weeks, the light spot and the light band with strong echo are seen in the lumen by the two-dimensional ultrasound, the vascular wall is obviously thickened and rough, the integrity is destroyed, the fibrosis is formed in the lumen, and the lumen is completely locked; d shows the vascular fibrosis at the postoperative 1 month. Table 1 shows the clinical data adopting the treatment method of this embodiment.

TABLE 1

Clinical data: 613 cases of the lower limb varicose vein (888 limbs)

| Sex | The number of cases | Age range | Average age | The lesion number of single lower limb varicose vein | The lesion number of double lower limb varicose vein |
|---|---|---|---|---|---|
| Female | 377 cases | 24-87 ages | 53.6 ages | 191 cases (191 limbs) | 176 cases (352 limbs) |
| Male | 246 cases | 25-83 ages | 51.5 ages | 147 cases (147 limbs) | 99 cases (198 limbs) | wherein, the whole group has the lower limb leg and/or thigh superficial venous obvious tortuous expansion or varicose into a group (occupy 93.2%, C2); 828 limbs (occupy 93.2%) has the lower limb soreness or heaviness (C2) after long standing long squatting at different degree; 356 limbs (occupy 40.1%) has the skin nutrition disorder on the thread area (C4); 115 limbs (occupy 13.0%) has leg ulcer (C5/C6). The treating effects by the ultrasound microwave treatment method are that: the lower extremity superficial varicose vein becomes flat: after surgery 613 cases in the whole group (888 limbs); the leg skin ulcer is healed: 115 limbs are healed for average 21.5d; the pigmentation is improved: 356 limbs are significantly regressed for average 32.6d; the soreness of the lower extremity and other symptoms are obviously improved: 828 limbs are improved at different degree.

Embodiment 2

Aiming at treating the lower limb perforating vein insufficiency (leg ulcers), the treatment method of this embodiment comprises steps as follows:

1. Pre-Operative Preparation:

1.1 Patient preparation: according to the lower limb perforating vein varicose degree and the general condition of the patient, select the anesthesia.

Figure 9:
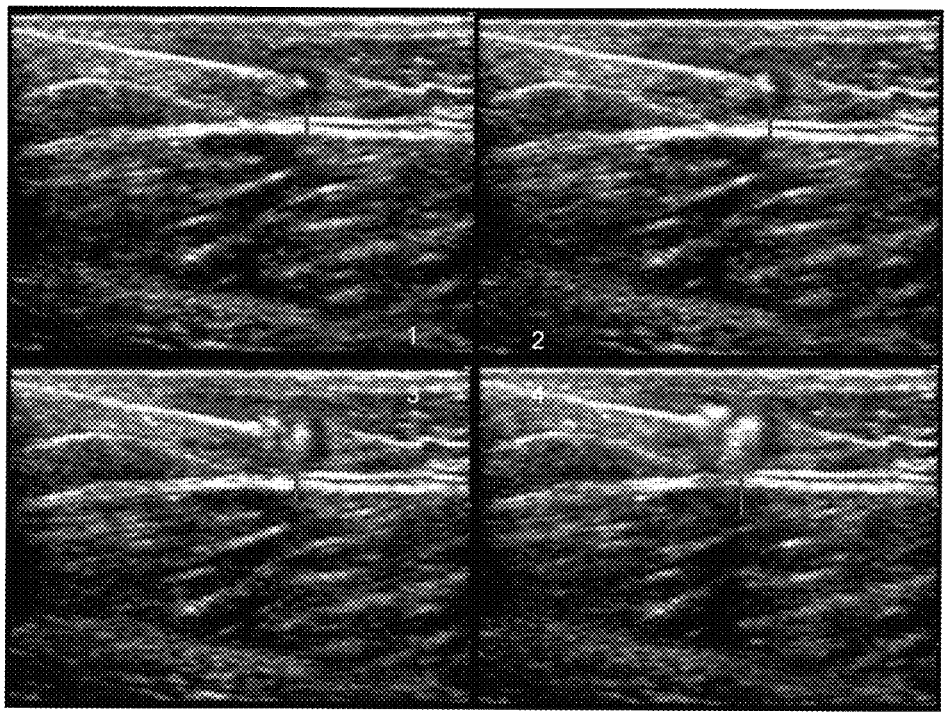
FIG. 9 is an effect drawing of treating the lower extremity perforating venous insufficiency by combining ultrasonic wave and microwave according to a second preferred embodiment of the present invention.

1.2 Instrument Preparation (1) Turn on the power supply of the ultrasound microwave therapeutic instrument, and check whether the device is in the normal state;

(2) Connect the therapeutic catheter with the microwave output terminal of the device via the microwave output cable, and connect the foot switch, and insert one end of the foot switch into the foot switch position of the microwave equipment;

(3) a) Tightly connect the in and out ports of the therapeutic needle refrigerant pipe with the in and out ports of the long water pipe, respectively; b) put the segment of the long water pipe with the steel needle at the left side of the pump head and insert the steel needle into the brine bottle (ice water below 15° C.), and hang the brine bottle at the side of the pump head upside down; c) 180°-anticlockwise flip the flipping rod on the pump head for opening the upper briquetting, naturally put the silicone tube in the long water pipe between the roller and the upper briquetting, 180°-clockwise flip the flipping rod for downwardly pressing the upper briquetting into place;

(4) Turn on the peristaltic pump switch and check whether the water cycle is normal;

2. Surgical Procedures:

Routinely clean and disinfect the lesion location of the patient in the supine position; puncture the short probe needle via the skin or from the superficial varicose vein (or normal skin puncture around the ulcer) into the lesion perforating branch vein under the guidance of ultrasound; depress the foot switch, instantly release the microwave energy with the power of 30-40 W at the 0.5-0.8 cm away from the deep vein edge, and gradually exit the needle towards the superficial direction, simultaneously continuously release microwave while exiting the needle, at the same time solidify close the superficial varicose vein, and monitor the treatment situation and closure effect of the varicose vein and the perforating branch vein during the whole course under the ultrasound real-time monitoring;

3. Postoperative Treatment:

Operation of lower limb superficial vein insufficiency; wear the elastic stockings after surgery, and then appropriately bandage the affected limb by the elastic bandage on the elastic stockings till postoperative 1 week, and then wear the elastic stockings for 1-2 months; after surgery, short-termly orally administrate enteric coated aspirin for 75-100 mg/d, decongestant diosmin, and activating blood anodyne; check D-dimer venous blood within preoperative and postoperative 1 week, reexamine the lower limb venous situation by color Doppler ultrasound. FIG. 9 is the effect drawing of integratedly treating the lower limb perforating venous insufficiency by the ultrasound microwave, wherein, 1 shows the short needle puncture pre-solidification during the surgery, and the arrow denotes the point of the short needle radiator; 2 shows that the short needle radiator begins to solidify, it can be seen that the small-scale solidification is around the point of the radiator by the arrow; 3 shows that the larger-scale solidification is around the point of the radiator by the arrow, the blood lumen is basically closed; 4 shows that the blood lumen is completely closed by the arrow. Table 2 shows the clinical data adopting the treatment method of this embodiment.

TABLE 2

Clinical data: 112 cases of the perforating venous insufficiency (112 limbs)

| Sex | The number of cases | Average age | Ulcer area | The number of ulcer | Bacterial infection |
|---|---|---|---|---|---|
| Female | 57 | 89 ages | <2 cm$^2$: 63 | 1:80 | 93 |
| Male | 55 | 59.48 ± 6 ages | ≥2 cm$^2$: 59 | >1:42 | (76.23%) |

The treatment effect by the ultrasonic wave and microwave treatment method: the improvement situation of the limb swelling: 95.00% (38/40); the improvement situation of the eczema-like change: 80.25% (65/81); the limb pigmentation change: 60.66% (74/122).

Now, evaluate the effects of the invention of this patent application from the following aspects:

1) Anesthesia and surgical time: the endovascular microwave solidification operation time of every limb is average 15 minutes, the anesthesia time is short, the anesthesia has less dosage, and the patient can rapidly recover;

2) The intraoperative bleeding is average 2.5 ml;

3) The improvement of the postoperative symptom of the patient, out of bed activity, the hospitalization time: the patient has no wound or lower limb pain, only postoperative few affected feet have the mild transient swelling, the patient can be out of bed activity by self after postoperative 1-2 hours, and the average hospitalization time is 5.3 days;

4) Appearance changes of the affected limb: the lower extremity varicose vein disappears, the clinical symptoms are significantly improved, the limb swelling is reduced, the pigmentation is gradually faded, the leg ulcer and the skin nutrition disorders are significantly improved or healed;

5) Complications and recurrence: no lower extremity deep venous thrombus or pulmonary embolism and other serious complications, the numbness of the postoperative leg skin is lighter, the average fading time is 2.5 months, and the recurrence ratio is lower and about 2% (which is lower than other methods);

6) The color Doppler ultrasound image change of the postoperative lower extremity proves that the treatment effect is good. At the postoperative day, the diameter of the great saphenous vein of the lower extremity is significantly narrowed, no blood flows, there are strongly echogenic thrombus light spot and light band within the lumen seen by two dimensional ultrasound, the blood vessel wall is obviously thickened and roughly, the integrity is destroyed, the fibrosis is formed within the above mentioned lumen at postoperative two weeks, and the internal of the lumen is completely closed.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for treating superficial venous insufficiency in a lower extremity of a patient, the method comprising:
finding a confluence of a femoral vein and a saphenous vein at a groin of an affected limb using ultrasound;
notching for 1-2 cm at a confluence or 0.5-1 cm at an ankle of the affected limb;
inserting, under guidance of a laser cursor, a microwave therapeutic probe into the saphenous vein either from 2 cm below a start of the saphenous vein at the confluence toward the ankle, or from the ankle toward the confluence in an event inserting from the 2 cm below the start of the saphenous vein is unable to be achieved;
selecting microwave transmission power in a range of 50-70 W and vein solidification time in a range of 5-10 s, the selecting being based upon an inner diameter of the saphenous vein of the affected limb and an amount of body fat of the patient; and
while monitoring with real-time ultrasound, applying treatment by solidifying the saphenous vein point-by-point with the microwave therapeutic probe and withdrawing the microwave therapeutic probe from the saphenous vein step-by-step; wherein:
the treatment is made intermittently at an interval of 1 cm, the microwave therapeutic probe being withdrawn while the saphenous vein is compressed by hand, so that a treated length of the saphenous vein is successively solidified and closed;
if said inserting of the microwave therapeutic probe is blocked by a blockage, a puncture is made along the saphenous vein beyond the blockage for anterogradely inserting the microwave therapeutic probe, so said treatment is made beyond the blockage; and
when a varicose conglobated branch vein is disposed along the saphenous vein, a respective vein puncture is made by the microwave therapeutic probe through the patient's skin while monitoring with real-time ultrasound and treatment of the varicose conglobated branch vein is made using a microwave transmit power in a range of 30-40 W by solidifying the branch vein point-by-point with the microwave therapeutic probe and withdrawing the microwave therapeutic probe from the branch vein.

2. The method, as recited in claim 1, further comprising a step of making a postoperative treatment comprising:
observing edema and pain of the affected limb and vital signs when surgery has been completed;
with the patient in a supine position, elevating the affected limb by 20-30 degrees so that the affected limb is elevated with respect to the patient's heart to aid blood return; bandaging with uniform pressure for avoiding hematocele and bleeding; extending and flexing the ankle so that deep venous blood is extruded by the patient's muscles to accelerate blood return and avoid forming deep venous thrombosis;
at 6 h after surgery, walking on flat ground out of bed for 1-2 h;
using anticoagulants to avoid forming postoperative thrombus; and
initially wearing elastic stockings while bandaging the affected limb using elastic bandages over the elastic stockings for the first 1-2 weeks after surgery, and then wearing the elastic stockings for the following 1-2 months.

* * * * *